US012758579B2

(12) United States Patent
Allison

(10) Patent No.: US 12,758,579 B2
(45) Date of Patent: *Oct. 13, 2026

(54) THERAPEUTIC METHOD OF USING A VETERINARY COMPOSITION TO PREVENT THE ONSET OF HORSE COLIC

(71) Applicant: Ashley Wolchina Allison, Daphne, AL (US)

(72) Inventor: Ashley Wolchina Allison, Daphne, AL (US)

( * ) Notice: Subject to any disclaimer, the term of this patent is extended or adjusted under 35 U.S.C. 154(b) by 245 days.

This patent is subject to a terminal disclaimer.

(21) Appl. No.: 18/639,927

(22) Filed: Apr. 18, 2024

(65) Prior Publication Data

US 2024/0261320 A1 Aug. 8, 2024

Related U.S. Application Data

(63) Continuation-in-part of application No. 17/949,576, filed on Sep. 21, 2022, now Pat. No. 11,986,492.

(51) Int. Cl.

*A61K 31/80* (2006.01)
*A61K 9/00* (2006.01)
*A61K 31/047* (2006.01)
*A61K 33/00* (2006.01)

(52) U.S. Cl.

CPC ............ *A61K 31/80* (2013.01); *A61K 9/0095* (2013.01); *A61K 31/047* (2013.01); *A61K 33/00* (2013.01)

(58) Field of Classification Search

CPC .... A61K 31/80; A61K 9/0095; A61K 31/047; A61K 33/00; A61K 47/26; A61K 47/46; A61K 9/0056; A61K 31/695; A23K 20/105; A23K 50/20

See application file for complete search history.

(56) References Cited

U.S. PATENT DOCUMENTS

| | | | | |
|---|---|---|---|---|
| 6,100,245 A * | 8/2000 | Sox | ........................... | A61P 1/04 514/156 |
| 2004/0202696 A1 | 10/2004 | Yamin | | |
| 2004/0259952 A1 | 12/2004 | Abbas | | |
| 2015/0010511 A1 | 1/2015 | Scetta | | |

OTHER PUBLICATIONS

Gas and discomfort under saddle. The Chronicle of the Horse. Published Jul. 17, 2019. Accessed Feb. 5, 2026. https://forum.chronofhorse.com/t/gas-and-discomfort-under-saddle/460076. (Year: 2019).*

Simethicone: Oral Paste. Wedgewood Pharmacy. Published Nov. 30, 2020 (as evidenced by Wayback Machine). Accessed Feb. 6, 2026. https://www.wedgewoodpharmacy.com/items/simethicone-oral-paste.html (Year: 2020).*

* cited by examiner

*Primary Examiner* — Sahana S Kaup
*Assistant Examiner* — Lucy M Tien
(74) *Attorney, Agent, or Firm* — H. Brock Kolls

(57) ABSTRACT

The present invention relates to a therapeutic method of using a veterinary composition to prevent the onset of horse colic that includes administering to a horse prior to or during stressful situations to prevent the onset of horse colic the veterinary composition of 50 to 100 parts per one hundred simethicone by volume and 0 to 50 parts per one hundred a palatant or sorbitol by volume. Dosage can be determined by body weight, ranging from 1 mL per 400 pounds of body weight to 1.2 mL per 400 pounds of body weight.

20 Claims, 3 Drawing Sheets

THERAPEUTIC METHOD OF USING A VETERINARY COMPOSITION TO PREVENT THE ONSET OF HORSE COLIC

CROSS-REFERENCE TO RELATED APPLICATIONS

This application contains subject matter that is related to the subject matter of the following co-pending application. The below-listed application is hereby incorporated herein by reference in its entirety:

This is a U.S. non-provisional application that is a continuation in part of a U.S. non-provisional application Ser. No. 17/949,576, inventor Ashley Wolchina Allison, entitled "ORAL SUPPLEMENT FOR PREVENTING COLIC IN HORSES", filed Sep. 21, 2022.

TECHNICAL FIELD OF THE INVENTION

The present invention relates to the prevention of gastrointestinal issues in animals and, more particularly, to an oral veterinary composition to prevent colic in horses. The oral veterinary composition can also be used in the treatment of colic in horses.

BACKGROUND OF THE INVENTION

Before our invention, colic was the leading cause of death in show horses. Treatments available for a horse suffering from colic are limited in number and are only available through expensive prescriptions or treatments given by a veterinarian. Often, the time required to obtain veterinary care can be several hours or longer, which may significantly increase mortality. There are few over-the-counter supplements available to prevent and no over the counter supplements available to treat colic in horses.

Simethicone is an anti-flatulence supplement frequently used to treat gastrointestinal issues in humans. Simethicone changes the surface tension of gas bubbles in the body, enabling their breakdown, which leads to the formation of larger bubbles. In this way, gas is eliminated more easily through belching or the passing of flatus.

Currently, there are no over-the-counter or prescription uses of simethicone for horses, and no efficient method of administering simethicone to horses.

As can be seen, there is a need for an over-the-counter, affordable, and effective means to treat and prevent colic in horses, which gives rise to the present invention.

SUMMARY OF THE INVENTION

The shortcomings of the prior art are overcome and additional advantages are provided through the provision of a therapeutic method of using a veterinary composition to prevent the onset of horse colic can comprise administering to a horse prior to or during stressful situations to prevent the onset of horse colic the veterinary composition of 50 to 99 parts per one hundred simethicone by volume and 1 to 50 parts per one hundred sorbitol by volume, wherein a dosage determined by body weight is from 1 mL per 400 pounds of body weight to 1.2 mL per 400 pounds of body weight.

Additional shortcomings of the prior art are overcome and additional advantages are provided through the provision of a therapeutic method of using a veterinary composition to prevent the onset of horse colic can comprise administering to a horse prior to or during stressful situations to prevent the onset of horse colic the veterinary composition of 50 to 99 parts per one hundred simethicone by volume and 1 to 50 parts per one hundred a palatant by volume, wherein a dosage determined by body weight is from 1 mL per 400 pounds of body weight to 1.2 mL per 400 pounds of body weight.

Additional shortcomings of the prior art are overcome and additional advantages are provided through the provision of a therapeutic method of using a veterinary composition to prevent the onset of horse colic can comprise administering to a horse prior to or during stressful situations to prevent the onset of horse colic the veterinary composition of 100 parts per one hundred simethicone by volume, wherein a dosage determined by body weight is from 1 mL per 400 pounds of body weight to 1.2 mL per 400 pounds of body weight.

Additional features and advantages are realized through the techniques of the present invention. Other embodiments and aspects of the invention are described in detail herein and are considered a part of the claimed invention. For a better understanding of the invention, with advantages and features, refer to the description and the drawings.

BRIEF DESCRIPTION OF THE FIGURES

The subject matter, which is regarded as the invention, is particularly pointed out and distinctly claimed in the claims at the conclusion of the specification. The foregoing and other objects, features, and advantages of the invention are apparent from the following detailed description taken in conjunction with the accompanying drawings, in which:

Figure 1:
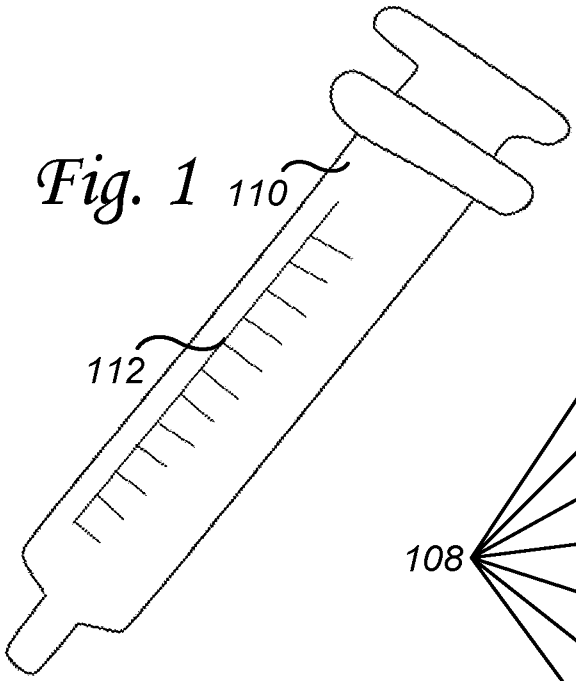
FIG. 1 illustrates one example of a front elevation view of an oral dosing syringe for use in a method of oral administration of a veterinary composition according to an embodiment of the present invention.

The detailed description explains the preferred embodiments of the invention, together with advantages and features, by way of example, with reference to the drawings.

DETAILED DESCRIPTION OF THE INVENTION

With regards to horses and preventing the onset of horse colic, which is the focus of the present invention, while the how or why of colic might not be fully understood, WHEN it might happen in horses is certainly predictable. This is why it is possible (and effective) to use the present invention as a preventative. In this regard, any stressful situation for a horse, such as extreme (or not so extreme) weather change, feed or hay change, new surroundings/farm, travel, competition, sickness, and other situations are all known triggers for colic in horses that are prone to it, and the treatment method of the present invention administered prior to or during stressful situations is effective in preventing the onset of horse colic.

Horses are notorious for colic and are predisposed to it when compared to other species. There are many factors that predispose horses to colic. Horse species have simple stomachs, unlike most other grazing animals, and are unable to vomit. They evolved grazing over most of their day but are now fed several large meals at once, morning and night. Horses also experience much more stress than their Mustang counterparts with their busy show and travel schedules. Most often, horses with colic have an overaccumulation of gas in their intestines ("gas colic") or a mild impaction. The cause is oftentimes undetermined but can be triggered by a change in feed, dental abnormalities, environmental stress ("change in the weather"), or transportation, to name a few.

An advantage, in the present invention, is that by understanding WHEN circumstances of stress for a horse will/are occurring and mitigating the risks of digestive stress by administering the therapeutic method of using the veterinary composition of the present invention, the onset of colic in horses can be prevented.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, an embodiment of the present invention provides a product that prevents and optionally treats colic in horses and a method of administering such a product. The invention may also be used to treat other animals or livestock such as dogs, cattle, pigs, sheep, donkeys, and others.

The product comprises simethicone, a surfactant polymer. Simethicone may be combined with oil or alcohol-based palatants such as sweeteners or other flavorings to form the product. These may include mint, apple, cinnamon, peppermint, banana, and other flavors. Simethicone may also be diluted with alcohol-based sweeteners such as sorbitol to increase palatability. Increasing the palatability of the product increases the likelihood that the horse or animal will ingest the product, thereby increasing the likelihood of effectively administering a dose to the animal.

The product may be provided in a liquid form and measured by a metered 112 syringe 110 or a metered 108 bottle 102. The liquid composition may be administered to the animal via an oral dosing syringe 110 directly into the animal's mouth when, for example, a horse is colicking and cannot take additional feed, or mixed with the animal's feed for use as a preventative before stressful events such as travel, competition, injury, feed changes, or abrupt weather changes.

Alternatively, the product may be provided in powder form. The powder composition may be mixed in or placed on top of the feed of the animal.

The volume of the product needed to dose the animal ranges from 0.1 milliliters to 10 milliliters. The low volume of the product in comparison to the feed of the animal enables easy consumption by the animal.

In an exemplary embodiment, a veterinary composition for preventing colic can comprise substantially 100% simethicone by volume. The veterinary composition can further comprise a range of 0.15 to 1 parts per one hundred of one or more of a palatant by volume. The palatant can be at least one of the following: mint, apple, cinnamon, peppermint, or banana.

In another exemplary embodiment, the veterinary composition can comprise about 50% to 75% simethicone by volume and about 25% to 50% sorbitol by volume. Sorbitol is effective because it dissolves in simethicone. The composition may further comprise palatants. The volume of the palatants is not particularly limited and may vary from about 0.01% to 1% by volume. In a preferred embodiment, the composition may comprise about 30 milliliters of simethicone, about 20 milliliters of sorbitol, and a palatable substance such as any of the following: about 3 drops (approximately 0.15 milliliters) of peppermint oil, about 10 drops (approximately 0.5 milliliters) of banana oil, or about 5 drops (approximately 0.25 milliliters) of cinnamon oil. For disclosure purposes, a drop is approximately 0.05 milliliters.

Dosages for the product are not particularly limited. In an ideal embodiment of the method of administering the product, the product is delivered during the feeding time of the animal. Dosages may increase at times of stress, such as weather changes, competition, or injury.

The dosage in milliliters may be determined by the weight of the animal in pounds, for example, as expressed in the following table.

| Weight in pounds | With Sorbitol, twice a day dosage in milliliters | Without Sorbitol, twice a day dosage in milliliters |
|---|---|---|
| 250-500 | 1.5 | 0.75 |
| 501-750 | 2 | 1.25 |
| 751-1000 | 2.5 | 1.5 |
| 1001-1250 | 3.5 | 2 |
| 1251-1500 | 4 | 2.25 |
| 1501-1750 | 4.5 | 2.75 |
| 1751-2000 | 5 | 3 |
| 2001-2250 | 6 | 3.5 |
| 2251-2500 | 6.5 | 3.75 |

Figure 5:
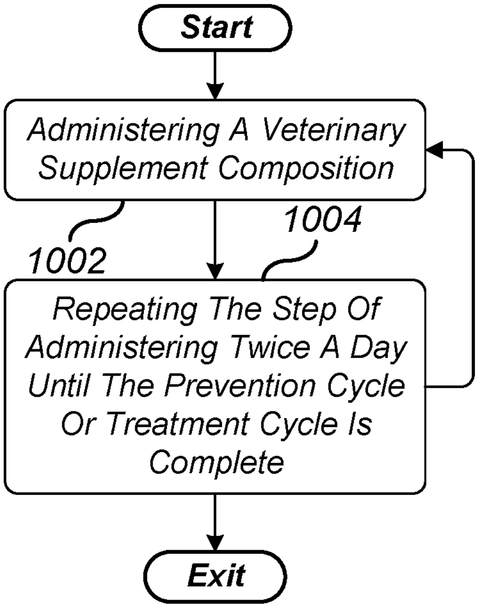
FIG. 5 illustrates one example of a therapeutic method of using a veterinary composition to prevent colic.

In an exemplary embodiment, with reference to FIG. 5, in step 1002, a veterinary composition of 50 to 75 parts per one hundred simethicone by volume and 25 to 50 parts per one hundred sorbitol by volume can be administered to an animal, wherein a dosage determined by body weight is 1 mL per 400 pounds of body weight to 1.2 mL per 400 pounds of body weight.

In an exemplary embodiment, in step 1004, the step of administering in 1002 can be repeated twice daily until the prevention cycle or treatment cycle is complete, or at other prescribed intervals as required. The treatment cycle can vary in duration from days to weeks, as required.

In another exemplary embodiment, a therapeutic method of using a veterinary composition to prevent the onset of horse colic can comprise in step 1002 administering to a horse prior to or during stressful situations to prevent the onset of horse colic the veterinary composition of 50 to 99 parts per one hundred simethicone by volume and 1 to 50 parts per one hundred sorbitol by volume, wherein a dosage determined by body weight is from 1 mL per 400 pounds of body weight to 1.2 mL per 400 pounds of body weight.

In another exemplary embodiment, a therapeutic method of using a veterinary composition to prevent the onset of horse colic can comprise in step 1002 administering to a horse prior to or during stressful situations to prevent the onset of horse colic the veterinary composition of 50 to 99 parts per one hundred simethicone by volume and 1 to 50 parts per one hundred a palatant by volume, wherein a dosage determined by body weight is from 1 mL per 400 pounds of body weight to 1.2 mL per 400 pounds of body weight.

In another exemplary embodiment, a therapeutic method of using a veterinary composition to prevent the onset of horse colic can comprise in step 1002 administering to a horse prior to or during stressful situations to prevent the onset of horse colic the veterinary composition of 100 parts per one hundred simethicone by volume, wherein a dosage determined by body weight is from 1 mL per 400 pounds of body weight to 1.2 mL per 400 pounds of body weight.

Referring to FIG. 1, there is illustrated a syringe 110 for use in a method of administering a horse colic treatment according to an embodiment of the present invention. The size of the oral dosing syringe 110 is not particularly limited. A scale indicia 112 can be visible on the body of the oral dosing syringe 110 and marked in a manner to inform how much of the veterinary composition volume is inside the oral dosing syringe 110. Such scale indicia 112 can be marked in milliliters or other units of measure, making it useful when measuring the proper dosage. In an exemplary embodiment, such scale indicia 112 can range from 1 milliliter to 12 milliliters, or other ranges or units of measure as required.

Figure 2:
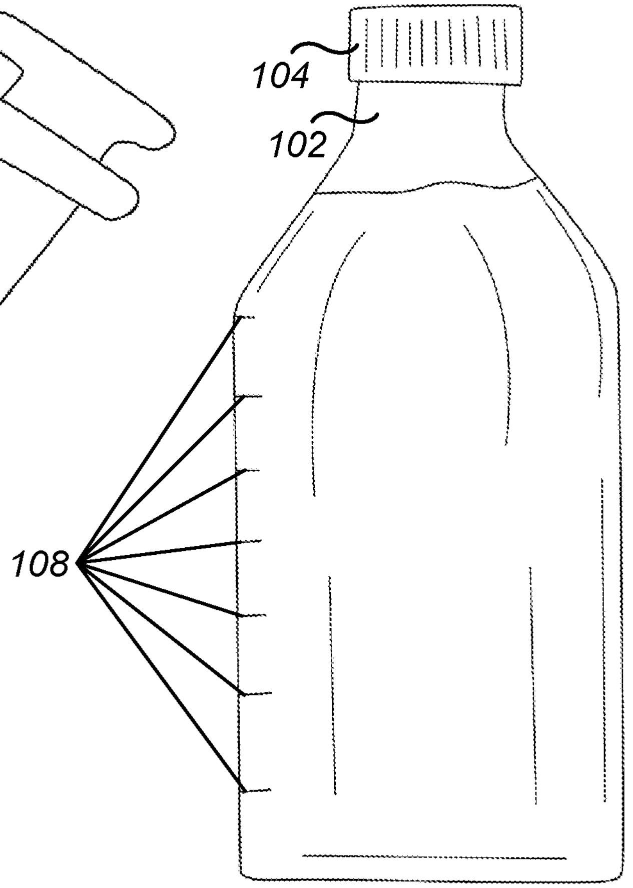
FIG. 2 illustrates one example of a front elevation view of a bottle for use with the veterinary.

Referring to FIG. 2, there is illustrated a bottle 102 for use in the present invention. The size, shape, and composition of bottle 102 are not particularly limited. In some embodiments, bottle 102 may be clear or amber and may be marked 108 to measure the amount of the liquid. Such markings 108 can be marked in milliliters or ounces, making it useful to determine how much of the veterinary composition remains in the bottle 102. In an exemplary embodiment, such markings 108 can range from 1 ounce to 7 ounces, or other ranges as required.

Figure 3:
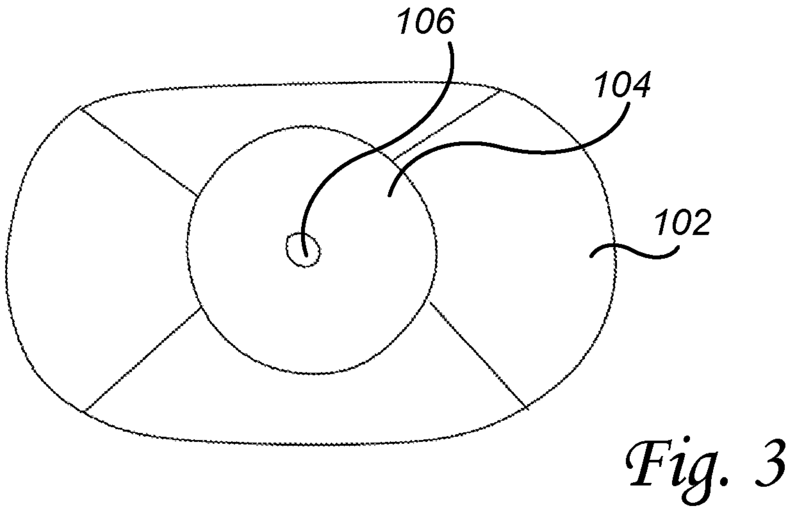
FIG. 3 illustrates one example of a top view of the bottle, showing an adapter.
Figure 4:
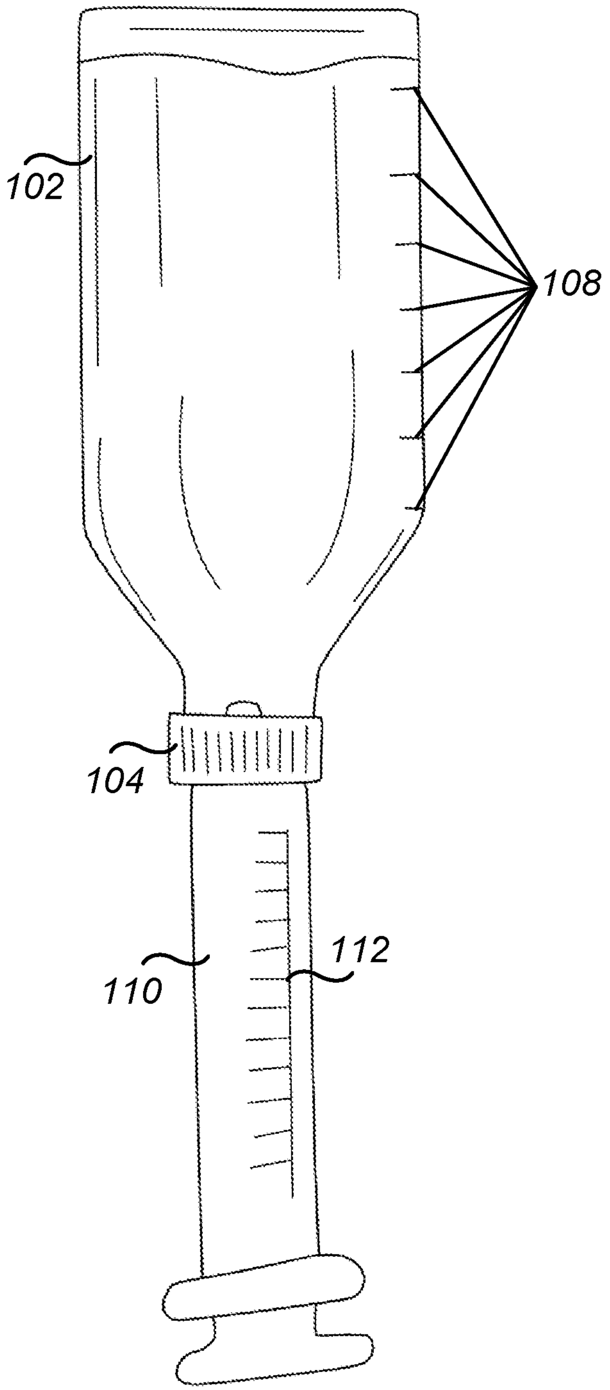
FIG. 4 illustrates one example of an inverted bottle with a temporarily interconnected oral dosing syringe.

Referring to FIG. 3, there is illustrated a top view of FIG. 2 that depicts the cap 104 used on the bottle 102. Cap 104 comprises adapter 106, which couples the oral dosing syringe 110 to bottle 102 without removal of cap 104 from bottle 102 to access the veterinary composition inside. In an exemplary embodiment, this allows the veterinary composition to be drawn from bottle 102 into oral dosing syringe 110 without the need to remove the cap 104, better protecting the hygiene and sterility of the veterinary composition within bottle 102 and making it easier to prepare a treatment dosage in the oral dosing syringe 110. FIG. 4 illustrates how the oral dosing syringe 110 interfaces with the adapter 106 and, in the inverted bottle 102 position, allows the oral dosing syringe 110 to draw the veterinary composition from bottle 102 in a measured treatment dosage within the oral dosing syringe 110.

Figure 6:
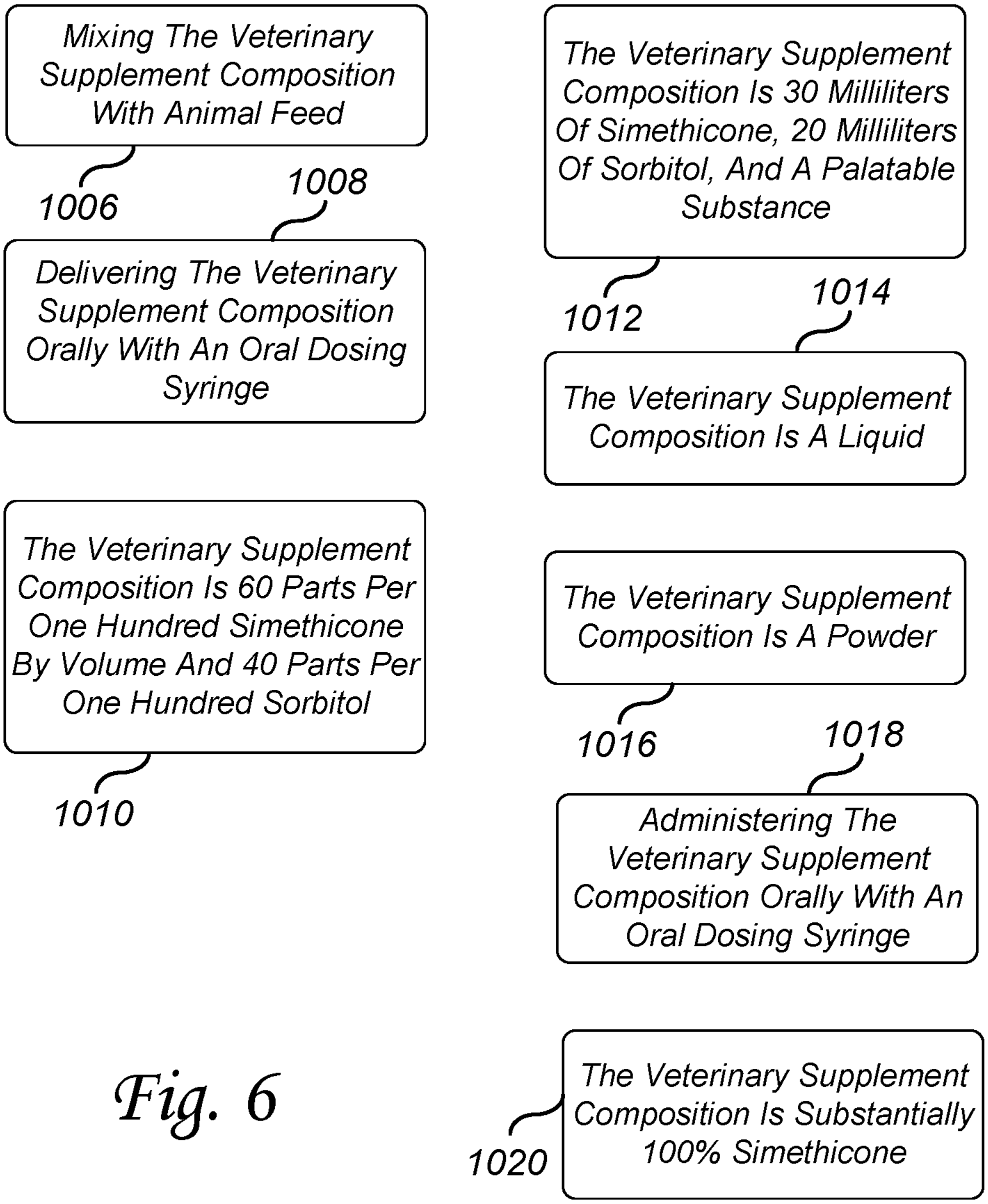
FIG. 6 illustrates exemplary embodiments that can be interchangeably used with the methods of the present invention.

Referring to FIG. 6, there are illustrated exemplary embodiments that can be interchangeably used with the methods of the present invention.

In step 1006, the veterinary composition can be mixed with animal feed.

In step 1008, the dosage of the veterinary composition can be delivered orally with an oral dosing syringe 110.

In step 1010, the veterinary composition can be 60 parts per one hundred simethicone by volume and 40 parts per one hundred sorbitol.

In step 1012, the veterinary composition can be 30 milliliters of simethicone, 20 milliliters of sorbitol, and a palatable substance of at least one of the following: 0.15 milliliters of peppermint oil, 0.5 milliliters of banana oil, or 0.25 milliliters of cinnamon oil.

In step 1014, the veterinary composition is a liquid.

In step 1016, the veterinary composition is a powder.

In step 1018, the veterinary composition is administered orally with an oral dosing syringe 110.

In step 1020, the veterinary composition is substantially 100% simethicone.

It should be understood, of course, that the foregoing relates to exemplary embodiments of the invention and that modifications may be made without departing from the spirit and scope of the invention as set forth in the following claims.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. A therapeutic method of using a veterinary composition to prevent the onset of horse colic, the method comprising the step of:

administering to a horse prior to or during stressful situations to prevent the onset of horse colic the veterinary composition of: 50 to 99 parts per one hundred simethicone by volume; and 1 to 50 parts per one hundred sorbitol by volume, wherein a dosage determined by body weight is from 1 mL per 400 pounds of body weight to 1.2 mL per 400 pounds of body weight.

2. The therapeutic method of claim 1, further comprising the step of:

repeating the step of administering twice a day.

3. The therapeutic method of claim 1, further comprising the step of:

mixing the veterinary composition with animal feed.

4. The therapeutic method of claim 1, further comprising:

delivering the dosage of the veterinary composition orally with an oral dosing syringe.

5. The therapeutic method of claim 1, wherein the veterinary composition is 99 parts per one hundred simethicone by volume and 1 parts per one hundred sorbitol.

6. The therapeutic method of claim 1, wherein the veterinary composition is a liquid.

7. The therapeutic method of claim 1, wherein the veterinary composition is a powder.

8. A therapeutic method of using a veterinary composition to prevent the onset of horse colic, the method comprising the step of:

administering to a horse prior to or during stressful situations to prevent the onset of horse colic the veterinary composition of: 99 to 99.85 parts per one hundred simethicone by volume; and 0.15 to 1 parts per one hundred a palatant by volume, wherein a dosage determined by body weight is from 1 mL per 400 pounds of body weight to 1.2 mL per 400 pounds of body weight.

9. The therapeutic method of claim 8, further comprising the step of:

repeating the step of administering twice a day.

10. The therapeutic method of claim 8, further comprising the step of:

mixing the veterinary composition with animal feed.

11. The therapeutic method of claim 8, further comprising:

delivering the dosage of the veterinary composition orally with an oral dosing syringe.

12. The therapeutic method of claim 8, wherein the palatant comprises 0.15 milliliters of peppermint oil, 0.5 milliliters of banana oil, or 0.25 milliliters of cinnamon oil.

13. The therapeutic method of claim 8, wherein the veterinary composition is a powder.

14. The therapeutic method of claim 8, wherein the palatant is at least one of the following: mint, apple, cinnamon, peppermint, or banana.

15. A therapeutic method of using a veterinary composition to prevent the onset of horse colic, the method comprising the steps of:

identifying an upcoming stressful event for a horse, the upcoming stressful event comprising travel, competition, injury, a feed change, or an abrupt weather change;

initiating administration of a dosage of the veterinary composition prior to the upcoming stressful event, wherein the veterinary composition consists of 100 parts per one hundred simethicone by volume; and continuing administration of the dosage during the upcoming stressful event to prevent the onset of horse colic, wherein the dosage is determined by body weight and is from 1 mL per 400 pounds of body weight to 1.2 mL per 400 pounds of body weight.

16. The therapeutic method of claim 15, further comprising the step of:

repeating the step of continuing administration twice a day.

17. The therapeutic method of claim 15, further comprising the step of:

mixing the veterinary composition with animal feed.

18. The therapeutic method of claim 15, further comprising:

delivering the dosage of the veterinary composition orally with an oral dosing syringe.

19. The therapeutic method of claim 15, wherein the veterinary composition is a liquid.

20. The therapeutic method of claim 15, wherein the veterinary composition is a powder.

* * * * *